United States Patent [19]
Nguyen et al.

[11] Patent Number: 5,944,700
[45] Date of Patent: Aug. 31, 1999

[54] ADJUSTABLE INJECTION LENGTH PEN NEEDLE

[75] Inventors: Tuan V. Nguyen, Rockaway; Michael A. Dibiasi, W. Milford, both of N.J.

[73] Assignee: Becton, Dickinson and Company, Franklin Lakes, N.J.

[21] Appl. No.: 08/938,271

[22] Filed: Sep. 26, 1997

[51] Int. Cl.[6] .................................................. A61M 5/00
[52] U.S. Cl. ........................ 604/263; 604/117; 604/192
[58] Field of Search .................................... 604/263, 192, 604/198, 187, 117, 110, 164, 165, 162

[56] References Cited

U.S. PATENT DOCUMENTS

| | | | |
|---|---|---|---|
| 4,897,083 | 1/1990 | Martell | 604/192 |
| 5,190,521 | 3/1993 | Hubbard et al. | 604/117 X |
| 5,336,199 | 8/1994 | Castillo et al. | 604/198 |

*Primary Examiner*—John D. Yasko
*Attorney, Agent, or Firm*—Alan W. Fiedler

[57] ABSTRACT

A pen needle of the present invention includes an extender that is rotatably attached to a hub on the pen needle to set the pen needle to a desired injection length. The extender is rotated into multiple predefined positions using a shield that is removably mounted on the pen needle. Each predefined position for the extender corresponds to a predetermined injection length for the pen needle such that the extender covers a section of the pen needle not being used for the injection. After the shield has been used to rotate the extender into one of the predefined positions the shield is removed from the pen needle to expose the distal point of the pen needle so that the injection can be performed.

9 Claims, 6 Drawing Sheets

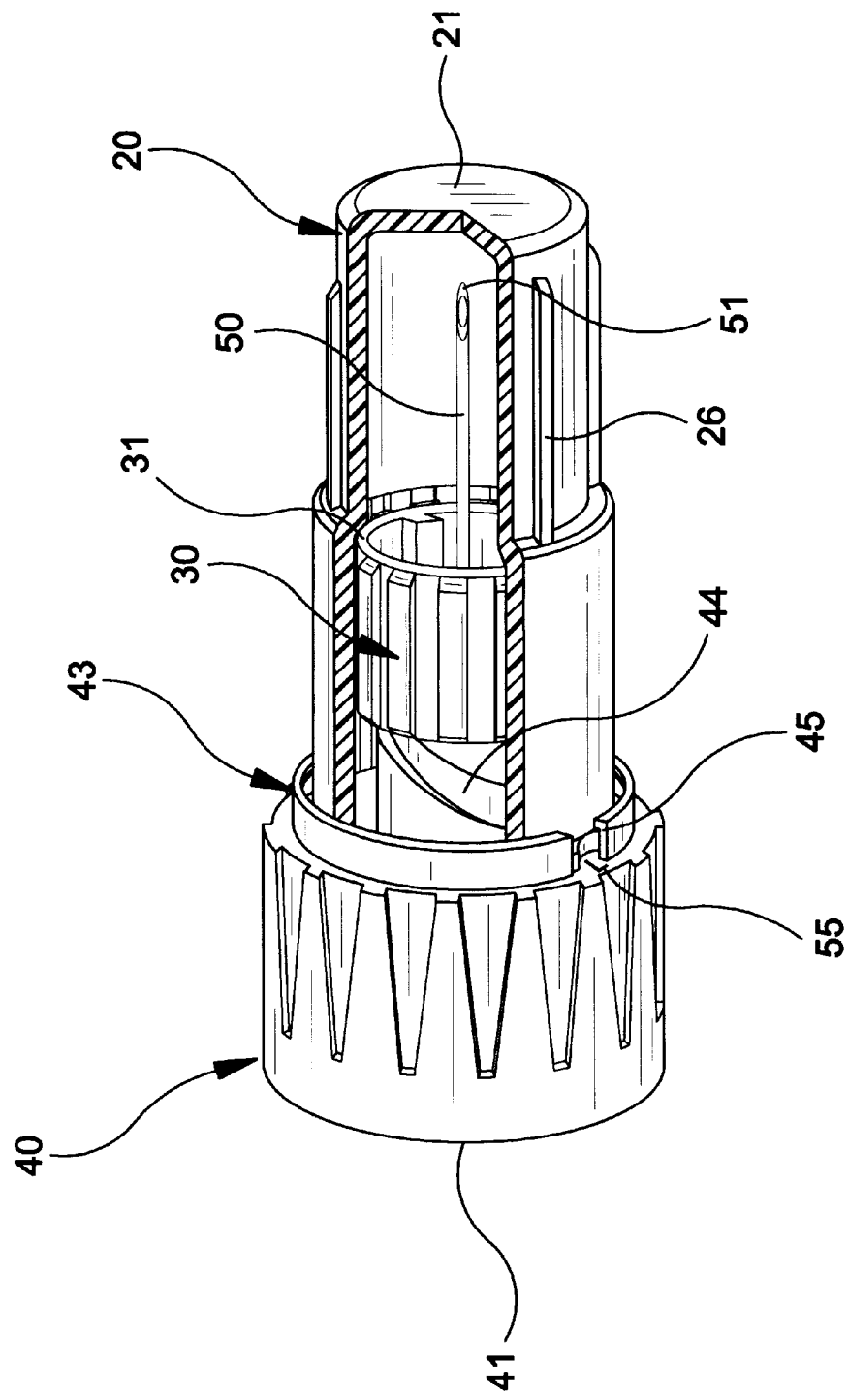

ADJUSTABLE INJECTION LENGTH PEN NEEDLE

BACKGROUND OF THE INVENTION

1. Field of the Invention

The subject invention relates to an adjustable injection length pen needle for use on a medication delivery pen having a cartridge assembly and a pen body assembly.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula is mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication is drawn into the chamber of the syringe barrel by moving the plunger a selected distance in a proximal direction. The needle cannula is withdrawn from the vial, and the medication is injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a cartridge holder into which a cartridge of insulin or other medication may be received. The cartridge holder is an elongate generally tubular structure with proximal and distal ends. The distal end of the prior art cartridge holder includes mounting means for engaging a double-ended needle cannula. The proximal end also includes mounting means for engaging a driver and dose setting apparatus as explained further below. A disposable cartridge for use with the prior art cartridge holder includes a distal end having a pierceable elastomeric seal that can be pierced by one end of the double-ended needle cannula. The proximal end of this prior art cartridge includes a plunger slideably disposed in fluid tight engagement with the cylindrical wall of the cartridge. This prior art medication delivery pen is used by inserting the cartridge of medication into the cartridge holder. A prior art pen body then is connected to the proximal end of the cartridge holder. The pen body includes a dose setting apparatus for designating a dose of medication to be delivered by the pen and a driving apparatus for urging the plunger of the cartridge distally for a distance corresponding to the selected dose.

The user of the pen mounts the double-ended needle cannula to the distal end of the cartridge holder such that the proximal point of the needle cannula pierces the elastomeric seal on the cartridge. The patient then selects a dose and operates the pen to urge the plunger distally to deliver the selected dose. The dose selecting apparatus then returns to zero upon injection of the selected dose. The patient then removes and discards the needle cannula, and keeps the prior art medication delivery pen in a convenient location for the next required medication administration. The medication in the cartridge will become exhausted after several such administrations of medication. The patient then separates the cartridge holder from the pen body. The empty cartridge may then be removed and discarded. A new cartridge can be inserted into the cartridge holder, and the cartridge holder and pen body can be reassembled and used as explained above.

The above described medication delivery pen is effective and much more convenient for self-administration of medication than the typical hypodermic syringe and separate medication vial. However, double-ended pen needles currently available are limited to specific injection lengths, i.e., 8 mm and 12.5 mm, that may not be the preferred lengths for all injections. In fact, many insulin pen users change their injection site from day to day or from site to site on their body on a regular basis. Therefore, there is the need for a pen needle that allows the insulin pen user to select the injection length according to the injection site on their body. In addition, such a pen needle would also be useful for families that have more than one insulin pen user with each pen user having a different body size and/or injection technique.

SUMMARY OF THE INVENTION

The subject invention relates to a pen needle for a medication delivery pen that overcomes the problems associated with current double-ended pen needles by providing a pen needle having an adjustable injection length.

The pen needle of the present invention includes an extender that is rotatably attached to a hub on the pen needle to set the pen needle to the desired injection length. The extender is rotated into multiple predefined positions using a separate shield that is removably mounted on the pen needle. Each predefined position for the extender corresponds to a predetermined injection length for the pen needle such that the extender covers a section of the pen needle not being used for the injection. After the shield has been used to rotate the extender into one of the predefined positions the shield is removed from the pen needle to expose the distal point of the pen needle so that the injection can be performed.

These and other aspects, features and advantages of the present invention will become apparent from the following detailed description taken in conjunction with the accompanying drawings.

DESCRIPTION OF THE DRAWINGS

FIG. 6 is a perspective and partial cross-sectional view of the pen needle assembly shown in FIG. 1 assembled and set to the shortest injection length.

DETAILED DESCRIPTION

Figure 1:
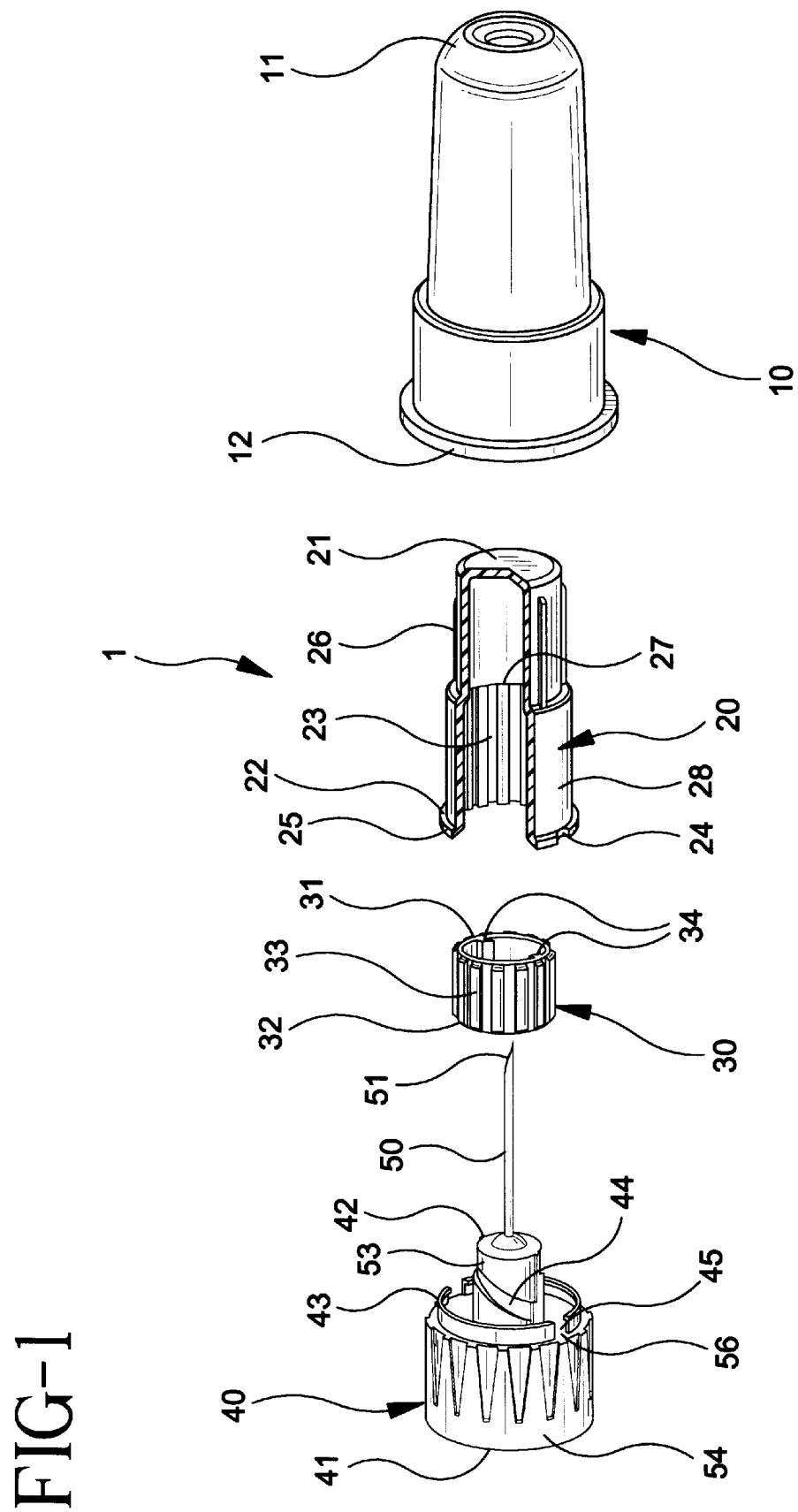
FIG. 1 is an exploded perspective view of a pen needle assembly according to the present invention.
Figure 2:
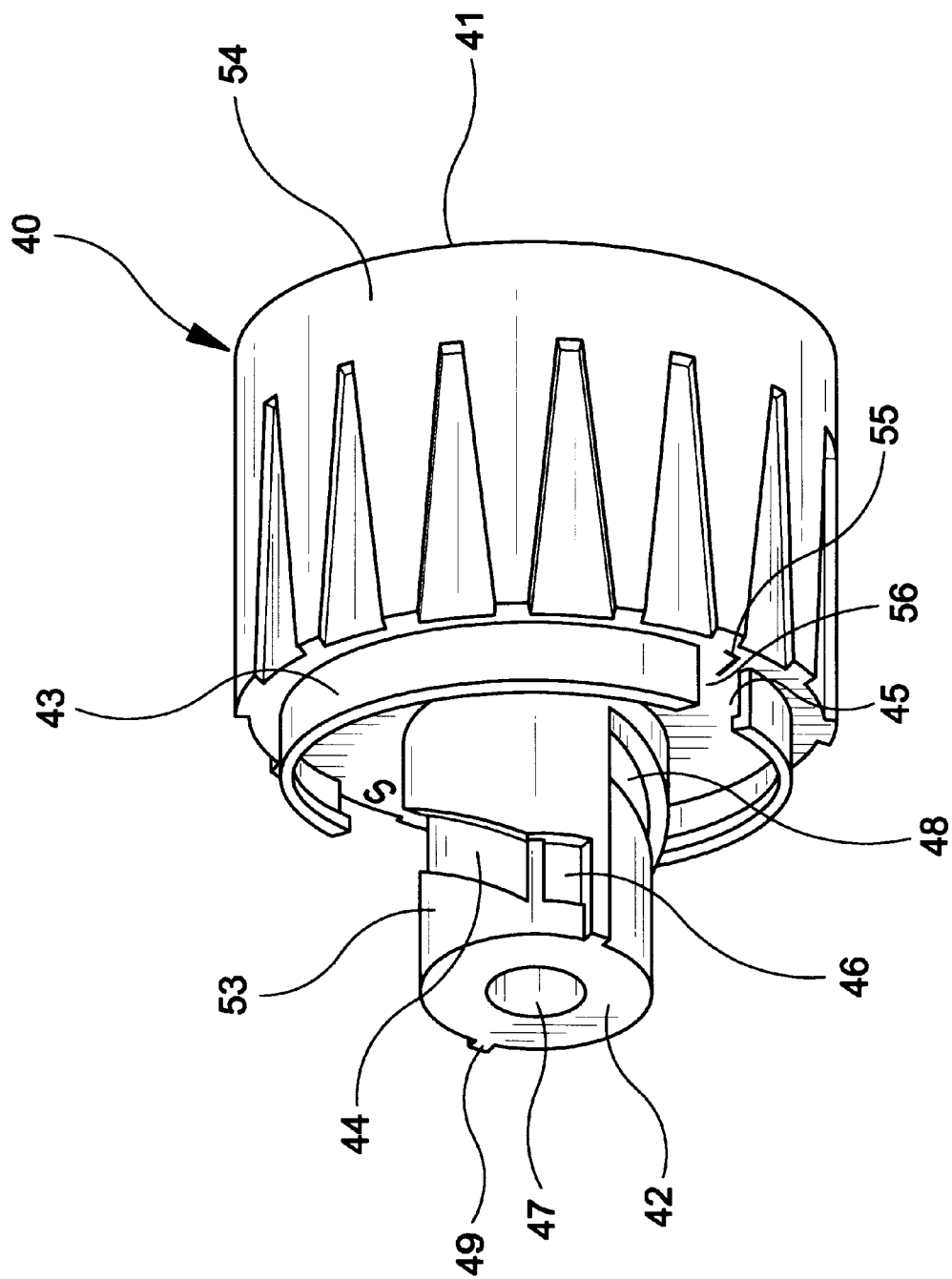
FIG. 2 is a perspective view of the pen needle hub in the pen needle assembly shown in FIG. 1.
Figure 3:
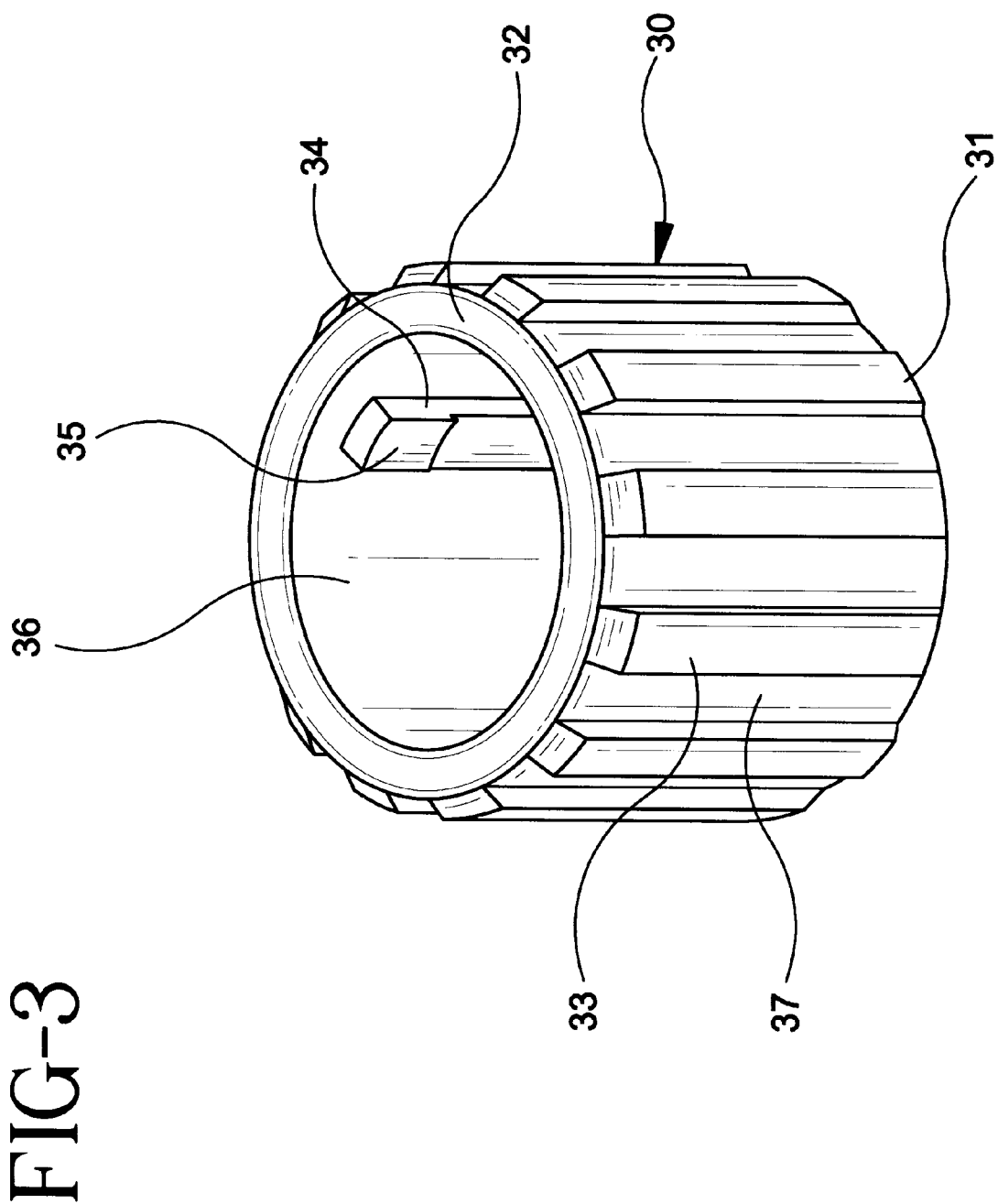
FIG. 3 is a perspective view of the extender in the pen needle assembly shown in FIG. 1.
Figure 4:
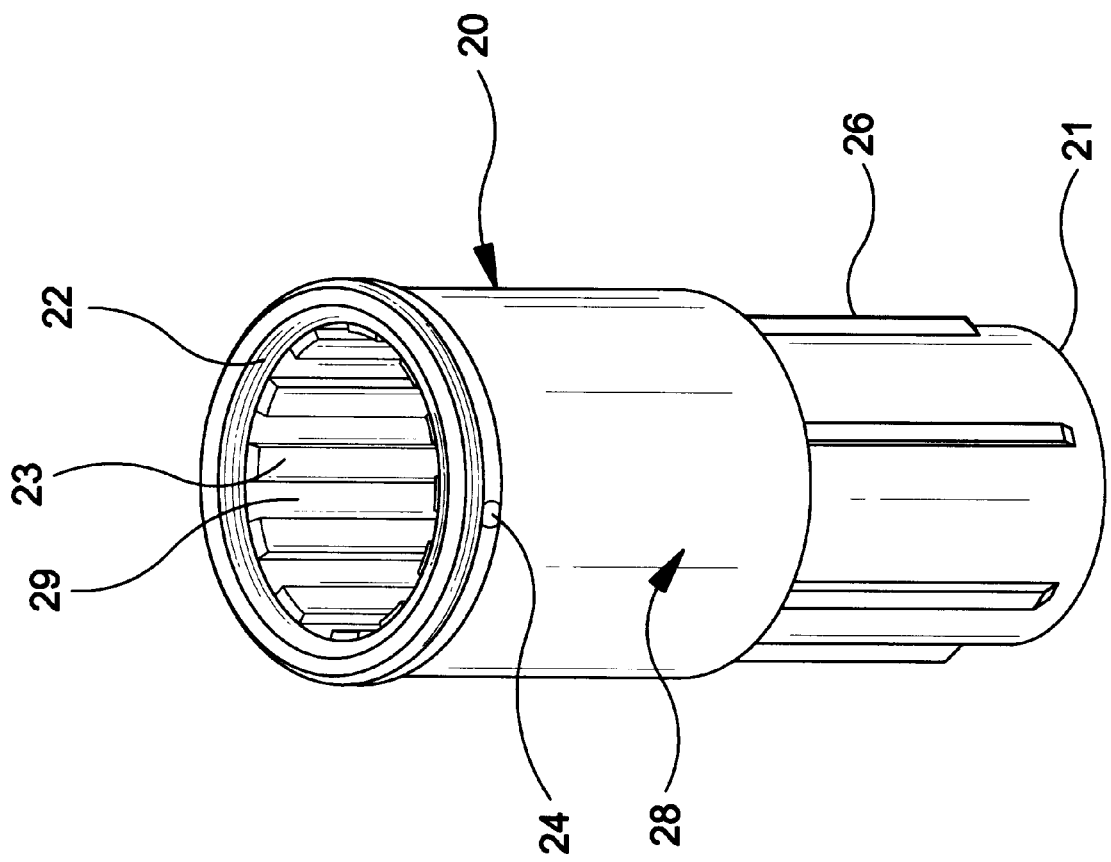
FIG. 4 is a perspective view of the shield in the pen needle assembly shown in FIG. 1.

A pen needle assembly in accordance with the subject invention is identified generally by the numeral 1 in FIG. 1. FIG. 1 shows an exploded perspective view of pen needle assembly 1 and its major components including an outer cover 10, a shield 20, an extender 30, and a pen needle hub 40 having a double-ended cannula 50. FIGS. 2–4 shows perspective views of pen needle hub 40, extender 30, and shield 20, respectively, in more detail.

Outer cover 10 includes a closed distal end 11 and an open proximal end 12 that removably mounts to pen needle hub 40 to cover cannula 50, shield 20 and extender 30 for shipping prior to use. Pen needle hub 40 includes an open proximal end 41 formed by a skirt 54 having dimensions and means for attaching pen needle hub 40 on the distal end of a conventional medication delivery pen like the one described above. As shown in FIGS. 1 and 2, pen needle hub 40 includes a distal surface 45 having a centrally located shaft 53 and a retention ring 43 extending therefrom. The inner surface of retention ring 43 is designed to mate with a flange 25 on proximal end 22 of shield 20, discussed further below. Retention ring 43 is shown in two sections that are separated at each end by a pair of openings 56 that are used to identify a long length injection setting and a short length injection setting, discussed further below. The long length injection setting and short length injection setting are also respectively identified by indicia 55, i.e., "L" and "S".

As shown in FIG. 2, shaft 53 includes a pair of ribs 49 set 180 degrees apart on the outer surface of shaft 53 and a pair of helical shaped grooves 44 extending from distal surface 45 to the distal end 42 of shaft 53. Grooves 44 from a helix profile of rib 49 to prevent extender 30 assembled on shaft 53 from disengaging from shaft 53 during the adjustment of the injection length by the user, as described below. Each groove 44 includes a slot 46 near distal end 42 of shaft 53 adjacent to one of the ribs 49 on the outer surface of shaft 53. Shaft 53 also includes a bore 47 through distal end 42 that receives double-ended cannula 50. Double-ended cannula 50 is epoxied or other wise permanently mounted therein so that distal point 51 extends from distal end 42 and a proximal point (not shown) extends into and is surrounded by skirt 54.

Extender 30 is generally cylindrical in shape with an open distal end 31 and an open proximal end 32. A pair of protrusions 34 are formed on an inner surface 36 of extender 30 and a plurality of splines 33 are formed on an outer surface 37 of extender 30. Each protrusion 34 extends from distal end 31 towards proximal end 32 and includes a boss 35 at its proximal end. When extender 30 is assembled onto shaft 53, boss 35 are aligned with grooves 44 on shaft 53 and ride in grooves 44 to the top of each groove 44. Each boss 35 then snaps into slot 46 at the end of groove 44 to prevent extender 30 from moving forward and disengaging off shaft 53 during the adjustment of the injection length and removal of shield 20, discussed further below. In other words, extender 30 is rotatably mounted on shaft 53 such that each boss 35 travels within one of said grooves 44 from a retracted position, shown in FIG. 5, where a long injection length is set, to an extended position, shown in FIG. 6, where a short injection length is set.

Figure 5:
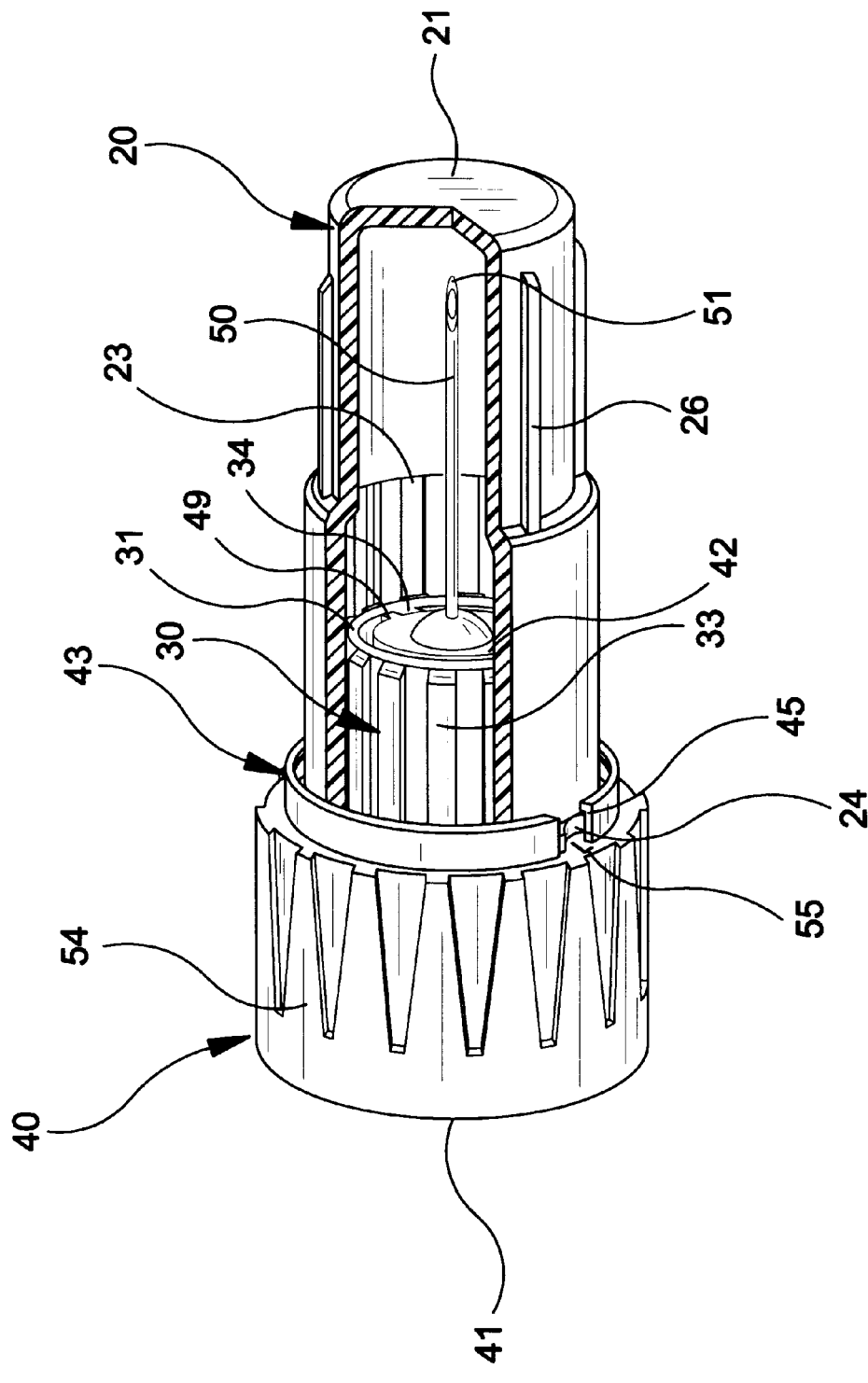
FIG. 5 is a perspective and partial cross-sectional view of the pen needle assembly shown in FIG. 1 assembled and set to the longest injection length.

When extender 30 is in the retracted position, shown in FIG. 5, each boss 35 is located at a proximal end 48 of groove 44 such that open distal end 31 is flush with distal end 42 of shaft 53. When extender 30 is in the retracted position, the full length of cannula 50 from where cannula 50 is attached to distal end 42 of shaft 53 to distal point 51 is available for the injection. However, when extender 30 is in the extended position, shown in FIG. 6, each boss 35 is received and held in slot 46 at the distal end of each groove 44 such that open distal end 31 of extender 30 extends beyond distal end 42 of shaft 53. When extender 30 is in the extended position, the usable length of cannula 50 is reduced to the length extending from distal end 31 of extender 30 to distal point 51 of cannula 50. Of course, multiple slots 46 could be positioned along each groove 44 to provide for two or more predefined injection lengths, for example, a pen needle having a long length of 12.7 mm, an intermediate length of 8 mm and a short length of 5 mm. Such an embodiment is also intended to be within the scope of the present invention.

The last major component of pen needle assembly 1 is shield 20. Shields are normally only used to protect the user from accidental needle sticks, however, shield 20 according to the present invention is designed for a second purpose. In the present invention, shield 20 is used to transfer radial torque to extender 30 and rotate extender 30 from and to different predefined injection lengths. Shield 20 includes a closed distal end 21 and an open proximal end 22 and is divided into two sections: a smaller diameter distal section 26 closed by distal end 21 and a larger diameter proximal section 28 connected to distal section 26 by a shelf 27. Open proximal end 22 leads to proximal section 28 and is surrounded by a flange 25 having a notch 24 that is selectively aligned with one of the openings 56 to identify whether extender 30 is in the extended position (designated by "S") or in the retracted position (designated by "L"). Flange 25 is also used to attach shield 20 to needle hub 40 by mating with the inside surface of retention ring 43 discussed above. When flange 25 on shield 20 bottoms out on distal surface 45 of needle hub 40, flange 25 snaps into retention ring 43 to hold shield 20 in place during the process of setting the injection length and is removed prior to injection. Proximal section 28 also includes a plurality of splines 23 on an inner surface 29 that mate with splines 33 on extender 30 to cause extender 30 to rotate on shaft 53 and move extender 30 from its retracted position to its extended position or from its extended position back to its retracted position.

To use pen needle assembly 1 of the present invention, the user would first remove a sterility barrier (not shown) from pen needle assembly 1 and use outer cover 10 as a tool to transfer radial torque to pen needle hub 40 to assemble pen needle assembly 1 onto a conventional medication delivery pen. After which outer cover 10 is removed from pen needle hub 40. The user then chooses the length of the needle they require for their injection, for example, long or short. In the present embodiment, injection length of pen needle assembly 1 is preset to the long injection length ("L"), shown in FIG. 5. Therefore, if the user wants a long length injection, there would be no need to change the length. It would only be necessary to remove shield 20 and perform the injection. However, if the user wants a short length injection needle, the user would rotate shield 20 and dial-in the desired injection length by rotating shield 20 until notch 24 on flange 25 aligns with the "S" on distal surface 45 of pen needle hub 40 (the position shown in FIG. 6). If the user then changes their mind and wants a long length injection needle, the user would rotate shield 20 in the other direction back to indicia "L", as shown in FIG. 5.

Current usable injection lengths for pen needles are 12.7 mm, 8 mm and 5 mm. Therefore, in a two-position pen needle assembly 1, like that shown in FIGS. 1–6, the injection lengths could have the following combinations:

| Long Injection Length (mm) | Short Injection Length (mm) |
|---|---|
| 12.7 | 8 |
| 8 | 5 |
| 12.7 | 5 |

While the invention has been described with respect to a preferred embodiment, it is apparent that various changes can be made without departing from the scope of the invention as defined by the appended claims. For example, various other long and short injection lengths could be used and more than two dialable settings could be used in a pen needle according to the present invention.

What is claimed is:

1. A pen needle assembly comprising:

a hub having an outer surface with a groove and a double-ended cannula having a distal point;

an extender movably mounted on said hub between a plurality of positions, said extender including an inner surface with a protrusion that travels in said groove as said extender moves between said plurality of position, wherein at each position said extender covers a predetermined portion of said cannula; and means for moving said extender on said hub between said plurality of positions.

2. A pen needle assembly according to claim 1, wherein said groove includes a slot for receiving said protrusion on said extender when said extender is at one of said plurality of positions.

3. A pen needle assembly according to claim 1, wherein:

said protrusion on said extender includes a boss extending from said protrusion into said extender; and said groove includes a slot for receiving said boss when said extender is at one of said plurality of positions.

4. A pen needle assembly according to claim 1, wherein said groove has a helical shape that causes said extender to rotate around said hub as said extender moves between said plurality of positions.

5. A pen needle assembly according to claim 4, wherein said extender further includes a spline on an outer surface that is used by said moving means to rotate said extender and move said extender between said plurality of positions.

6. A pen needle assembly according to claim 5, wherein said means for moving said extender on said hub includes a shield having an internal spline that mates with said spline on said extender to rotate said extender and move said extender between said plurality of positions.

7. A pen needle assembly according to claim 6, wherein said hub further includes a retaining ring for rotatably mounting said shield on said hub to shield said distal point of said cannula and permit said shield to be rotated on said hub and rotate said extender between said plurality of positions.

8. A pen needle assembly according to claim 7, further comprising an outer cover that receives said hub to cover said cannula, said extender and said shield prior to using said pen needle assembly.

9. A pen needle assembly according to claim 1, wherein said means for moving said extender on said hub includes a shield that mates with said extender to move said extender between said plurality of positions.

\* \* \* \* \*